United States Patent [19]

Doria et al.

[11] Patent Number: 4,522,944
[45] Date of Patent: Jun. 11, 1985

[54] CARBOXAMIDO-DERIVATIVES OF 5H-1,3,4-THIADIAZOLO[3,2-A]PYRIMIDINES, COMPOSITIONS AND USE

[76] Inventors: Gianfederico Doria, via L. Pasteur 16, Milan; Carlo Passarotti, via Fiume 2, Gallarate (Varese); Ada Buttinoni, via Monte Suello 18, Milan, all of Italy

[21] Appl. No.: 559,322

[22] Filed: Dec. 8, 1983

[30] Foreign Application Priority Data

Dec. 23, 1982 [GB] United Kingdom ............... 8236642
Nov. 8, 1983 [GB] United Kingdom ............... 8329746

[51] Int. Cl.³ ............... A61K 31/505; A61K 31/535; C07D 513/04
[52] U.S. Cl. ............... 514/222; 514/231; 514/258; 544/58.2; 544/58.6; 544/117; 544/255
[58] Field of Search ............... 544/58.2, 58.6, 117, 544/255; 424/246, 248.51, 251

[56] References Cited

FOREIGN PATENT DOCUMENTS 847698 5/1976 Belgium.
5028439 12/1970 Japan.
7142989 2/1981 Japan.

OTHER PUBLICATIONS

Chemical Abstract—vol. 76, 1972, #59562g.
Chemical Abstract—vol. 84, 1976, #84:4010k.

Primary Examiner—Robert W. Ramsuer
Attorney, Agent, or Firm—Murray, Whisenhunt & Ferguson

[57] ABSTRACT

The present invention relates to new carboxamido-derivatives of 5H-1,3,4-thiadiazolo[3,2-a]pyrimidines, to a process for their preparation and to pharmaceutical (i.e. anti-inflammatory and analgesic) compositions containing them.

The invention provides compounds having the following general formula (I)

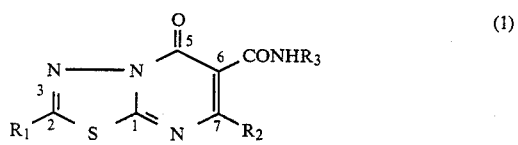

wherein
$R_1$ represents:
(a) a hydrogen or halogen atom or a $C_1$-$C_6$ alkyl group unsubstituted or substituted by $C_1$-$C_6$ alkoxy;
(b) a

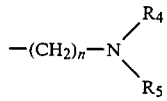

group, wherein n is zero, 1, 2 or 3 and each of $R_4$ and $R_5$ is, independently, hydrogen or $C_1$-$C_6$ alkyl, or $R_4$ and $R_5$, taken together with the nitrogen atom to which they are linked, form an unsubstituted N-pyrrolidinyl ring or a piperidino, morpholino, N-piperazinyl or

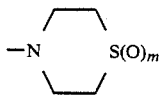

ring, wherein m is zero, 1 or 2, the piperidino and morpholino rings are unsubstituted or substituted by one or two $C_1$-$C_6$ alkyl groups and the N-piperazinyl ring is unsubstituted or substituted by a substituent chosen from $C_1$-$C_6$ alkyl, phenyl and pyridyl;
(c) trihalomethyl or a $R_6$—$S(O)_p$— group, wherein p is zero, 1 or 2 and $R_6$ is $C_1$-$C_6$ alkyl or benzyl, wherein the phenyl ring is unsubstituted or substituted by a substituent chosen from halogen, $C_1$-$C_6$ alkyl and $C_1$-$C_6$ alkoxy; or
(d) an unsubstituted pyridyl, pyridyl-N-oxide or thienyl ring or a phenyl ring unsubstituted or substituted by one, two or three substituents independently chosen from halogen, $C_1$-$C_6$ alkyl, $C_1$-$C_6$ alkoxy, hydroxy, formyloxy, $C_2$-$C_8$ alkanoyloxy, nitro, amino, formylamino, $C_2$-$C_8$ alkanoylamino and di-($C_1$-$C_6$) alkyl-amino;
$R_2$ represents a hydrogen atom or a $C_1$-$C_6$ alkyl group;
$R_3$ represents:
(a') a phenyl ring, unsubstituted or substituted by one or two substituents independently chosen from $C_1$-$C_6$ alkyl, $C_1$-$C_6$ alkoxy and halogen;
(b') an unsaturated heteromonocyclic or heterobicyclic ring, containing one or more heteroatoms chosen from nitrogen and sulphur, unsubstituted or substituted by one or two substituents independently chosen from halogen, $C_1$-$C_6$ alkyl and $C_1$-$C_6$ alkoxy; and the pharmaceutically acceptable salts thereof.

7 Claims, No Drawings"

CARBOXAMIDO-DERIVATIVES OF 5H-1,3,4-THIADIAZOLO[3,2-A]PYRIMIDINES, COMPOSITIONS AND USE

The present invention includes also the metabolites and the metabolic precursors of the compounds of formula (I) and all the possible isomers of the compounds of formula (I), e.g. optical isomers, and mixtures thereof. The alkyl, alkoxy, alkylthio, alkylsulfinyl, alkylsulfonyl, alkanoyloxy and alkanoylamino groups may be branched or straight chain groups.

A halogen atom is, for example, chlorine, bromine or fluorine, preferably it is chlorine or fluorine. A trihalomethyl group is preferably trifluoromethyl. A $C_1$–$C_6$ alkyl group is preferably a $C_1$–$C_4$ alkyl group, in particular methyl, ethyl, propyl, isopropyl, butyl and tert-butyl.

A $C_1$–$C_6$ alkoxy group is preferably a $C_1$–$C_4$ alkoxy group, in particular, methoxy, ethoxy, propoxy and isopropoxy. A $C_1$–$C_6$ alkylthio group is, for example, methylthio, ethylthio, propylthio, butylthio; preferably it is methylthio, ethylthio and propylthio.

A $C_1$–$C_6$ alkylsulfinyl is, for example, methylsulfinyl, ethylsulfinyl and propylsulfinyl.

A $C_1$–$C_6$ alkylsulfonyl, is for example, methylsulfonyl, ethylsulfonyl and propylsulfonyl.

A $C_2$–$C_8$ alkanoyloxy group is, for example, acetoxy, propionyloxy, butyryloxy and valeryloxy; preferably it is acetoxy.

A $C_2$–$C_8$ alkanoylamino group is, for example, acetylamino, propionylamino, butyrylamino; preferably it is acetylamino. When $R_1$ represents an unsubstituted $C_1$–$C_6$ alkyl group, it is, e.g. methyl, ethyl, propyl, isopropyl, butyl or tert-butyl; preferably it is methyl, ethyl or isopropyl. When $R_1$ is a substituted $C_1$–$C_6$ alkyl group, as defined above under (a), it is preferably $C_1$–$C_4$ alkyl substituted by $C_1$–$C_4$ alkoxy, more preferably by methoxy or ethoxy. When $R_1$ is a

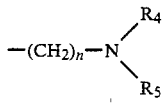

group, wherein n is as defined above and $R_4$ and $R_5$, being the same or different, are $C_1$–$C_6$ alkyl, preferably $R_4$ and $R_5$ are $C_1$–$C_4$ alkyl, more preferably ethyl, propyl and isopropyl.

When $R_4$ and $R_5$, taken together with the nitrogen atom to which they are linked, form a piperidino or morpholino ring, said ring, when substituted, is preferably substituted by one or two $C_1$–$C_4$ alkyl groups, which may be the same or different; more preferably it is substituted by a substituent chosen from methyl, ethyl, propyl and isopropyl.

When $R_4$ and $R_5$, taken together with the nitrogen atom to which they are linked, form a N-piperazinyl ring, said ring, when substituted, is preferably substituted by a substituent chosen from phenyl, pyridyl and $C_1$–$C_4$ alkyl, e.g. methyl, ethyl, propyl, isopropyl, butyl, tert-butyl.

When $R_2$ represents a $C_1$–$C_6$ alkyl group, it is, e.g. methyl ethyl, propyl, isopropyl, butyl or tert-butyl; preferably it is methyl, ethyl or isopropyl.

When $R_1$ and/or $R_3$ is a phenyl ring as defined above under (d) and (a'), respectively, said ring is preferably substituted by one or two substituents chosen from chlorine, fluorine, methyl and methoxy.

When $R_6$ is a benzyl group substituted as defined above, it is preferably substituted by a substituent chosen from chlorine, methyl and methoxy.

When $R_3$ is an unsaturated heteromonocyclic or heterobicyclic ring as defined above under (b'), it is, for example, a ring chosen from pyridyl, thiazolyl, pyrazolyl, pyrimidinyl and benzothiazolyl; preferably it is a thiazolyl or pyridyl ring wherein the thiazolyl and pyridyl rings are unsubstituted or substituted by one or two substituents chosen from methyl, chlorine, bromine and methoxy or it is a pyrazolyl ring substituted by a $C_1$–$C_4$ alkyl group.

Preferred compounds of the invention are the compounds having formula (I),
wherein
$R_1$ is
(a'') hydrogen, $C_1$–$C_3$ alkyl, $C_1$–$C_3$ alkylthio, benzylthio, methoxymethyl, ethoxymethyl or di-($C_1$–$C_4$ alkyl)amino; or
(b'') an unsubstituted N-pyrrolidinyl ring; a morpholino or piperidino ring, both unsubstituted or substituted by $C_1$–$C_2$ alkyl; or a N-piperazinyl ring substituted by a substituent chosen from $C_1$–$C_3$ alkyl, phenyl and pyridyl; or
(c'') an unsubstituted pyridyl or pyridyl-N-oxide ring; or a phenyl ring unsubstituted or substituted by one or two substituents chosen from chlorine, fluorine and methyl; or
(d'') a

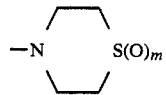

ring, wherein m is zero, 1 or 2;
$R_2$ is hydrogen or $C_1$–$C_2$ alkyl;
$R_3$ is an unsubstituted benzothiazolyl ring; 1-($C_1$–$C_4$ alkyl)pyrazolyl; or a thiazolyl or pyridyl ring, both unsubstituted or substituted by one or two substituents chosen from methyl and chlorine; and the pharmaceutically acceptable salts thereof.

More preferred compounds of the invention are the compounds having formula (I),
wherein
$R_1$ is
(a''') hydrogen or methyl; or
(b''') an unsubstituted N-pyrrolidinyl ring; a piperidino or a morpholino ring, both unsubstituted or substituted by $C_1$–$C_2$ alkyl; or a N-piperazinyl ring substituted by a substituent chosen from $C_1$–$C_3$ alkyl, phenyl and pyridyl; or
(c''') an unsubstituted pyridyl or pyridyl-N-oxide ring; or
(d''') a

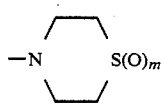

ring, wherein m is zero, 1 or 2;
$R_2$ is hydrogen or methyl;
$R_3$ is an unsubstituted benzothiazolyl ring; 1-($C_1$–$C_2$-alkyl)-pyrazolyl; or a thiazolyl or pyridyl ring, both unsubstituted or substituted by one or two methyl groups; and the pharmaceutically acceptable salts thereof.

Examples of pharmaceutically acceptable salts are those with inorganic acids, e.g., nitric, hydrochloric, hydrobromic and sulphuric acids and with organic acids, e.g., citric, tartaric, maleic, malic, fumaric, methanesulphonic and ethanesulphonic acids.

Examples of particularly preferred compounds of the invention are:

5-oxo-5H-1,3,4-thiadiazolo[3,2-a]pyrimidine-6-N-(2-pyridyl)-carboxamide;

5-oxo-5H-1,3,4-thiadiazolo[3,2-a]pyrimidine-6-N-(2-thiazolyl)-carboxamide;

2-(4-pyridyl)-5-oxo-5H-1,3,4-thiadiazolo[3,2-a]pyrimidine-6-N-(2-benzothiazolyl)-carboxamide;

2-morpholino-5-oxo-5H-1,3,4-thiadiazolo[3,2-a]pyrimidine-6-N-(2-benzothiazolyl)-carboxamide;

2-morpholino-5-oxo-5H-1,3,4-thiadiazolo[3,2-a]pyrimidine-6-N-(2-thiazolyl)-carboxamide;

2-methyl-5-oxo-5H-1,3,4-thiadiazolo[3,2-a]pyrimidine-6-N-(2-pyridyl)-carboxamide;

2-morpholino-5-oxo-5H-1,3,4-thiadiazolo[3,2-a]pyrimidine-6-N-(2-pyridyl)-carboxamide;

5-oxo-5H-1,3,4-thiadiazolo[3,2-a]pyrimidine-6-N-(2-benzothiazolyl)-carboxamide;

2-(3-pyridyl)-5-oxo-5H-1,3,4-thiadiazolo[3,2-a]pyrimidine-6-N-(2-pyridyl)-carboxamide;

2-(4-pyridyl)-5-oxo-5H-1,3,4-thiadiazolo[3,2-a]pyrimidine-6-N-(2-pyridyl)-carboxamide;

2-(4-pyridyl)-5-oxo-5H-1,3,4-thiadiazolo[3,2-a]pyrimidine-6-N-(2-thiazolyl)-carboxamide;

2-(2-methyl-morpholino)-5-oxo-5H-1,3,4-thiadiazolo[3,2-a]pyrimidine-6-N-(2-pyridyl)-carboxamide;

2-(4-methyl-piperazin-1-yl)-5-oxo-5H-1,3,4-thiadiazolo[3,2-a]pyrimidine-6-N-(2-pyridyl)-carboxamide;

2-(4-pyridyl)-5-oxo-5H-1,3,4-thiadiazolo[3,2-a]pyrimidine-6-N-(4-methyl-2-thiazolyl)-carboxamide;

2-(2-methyl-morpholino)-5-oxo-5H-1,3,4-thiadiazolo[3,2-a]pyrimidine-6-N-(2-thiazolyl)-carboxamide;

2-thiomorpholino-5-oxo-5H-1,3,4-thiadiazolo[3,2-a]pyrimidine-6-N-(2-pyridyl)-carboxamide;

7-methyl-2-morpholino-5-oxo-5H-1,3,4-thiadiazolo[3,2-a]pyrimidine-6-N-(2-pyridyl)-carboxamide;

7-methyl-2-morpholino-5-oxo-5H-1,3,4-thiadiazolo[3,2-a]pyrimidine-6-N-(2-thiazolyl)-carboxamide;

7-methyl-5-oxo-5H-1,3,4-thiadiazolo[3,2-a]pyrimidine-6-N-(2-pyridyl)-carboxamide;

7-methyl-5-oxo-5H-1,3,4-thiadiazolo[3,2-a]pyrimidine-6-N-(2-thiazolyl)-carboxamide;

2-(3-pyridyl-N-oxide)-5-oxo-5H-1,3,4-thiadiazolo[3,2-a]pyrimidine-6-N-(2-pyridyl)-carboxamide;

2-(4-pyridyl-N-oxide)-5-oxo-5H-1,3,4-thiadiazolo[3,2-a]pyrimidine-6-N-(2-thiazolyl)-carboxamide;

2-thiomorpholino-5-oxo-5H-1,3,4-thiadiazolo[3,2-a]pyrimidine-6-N-(2-thiazolyl)-carboxamide;

7-methyl-2-(3-pyridyl)-5-oxo-5H-1,3,4-thiadiazolo[3,2-a]pyrimidine-6-N-(2-pyridyl)-carboxamide;

7-methyl-2-(4-pyridyl)-5-oxo-5H-1,3,4-thiadiazolo[3,2-a]pyrimidine-6-N-(2-thiazolyl)-carboxamide;

2-(thiomorpholino-1,1-dioxide)-5-oxo-5H-1,3,4-thiadiazolo[3,2-a]pyrimidine-6-N-(2-pyridyl)-carboxamide;

2-(thiomorpholino-1,1-dioxide)-5-oxo-5H-1,3,4-thiadiazolo[3,2-a]pyrimidine-6-N-(2-thiazolyl)-carboxamide;

and the pharmaceutically acceptable salts thereof.

The compounds of this invention can be prepared by a process comprising reacting a compound of formula (II)

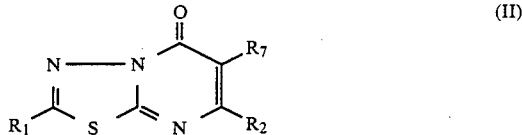

wherein $R_1$ and $R_2$ are as defined above and $R_7$ is carboxy or a reactive derivative of a carboxy group, with a compound of formula (III)

wherein $R_3$ is as defined above; and if desired, converting a compound of formula (I) into another compound of formula (I) and/or, if desired, converting a compound of formula (I) into a pharmaceutically acceptable salt thereof and/or, if desired, obtaining a free compound of formula (I) from a salt thereof and/or, if desired, separating a mixture of isomers into the single isomers.

When $R_7$ is a reactive derivative of a carboxy group, it is preferably a carboxylic ester, for example, a group of formula —$COR'_7$, wherein $R'_7$ is, e.g., $C_1$-$C_{12}$ alkoxy or tri($C_1$-$C_6$)-alkyl-silyloxy. The reaction between a compound of formula (II), wherein $R_7$ is a —$COR'_7$ group wherein $R'_7$ is $C_1$-$C_{12}$ alkoxy or tri($C_1$-$C_6$)-alkyl-silyloxy, and a compound of formula (III) may be carried out, for example, by heating with polyphosphoric or methanesulphonic or p-toluenesulphonic acid at a temperature varying between about 50° C. and about 200° C. in the absence of a solvent or in the presence of an inert organic solvent such as dimethylformamide, dimethylacetamide, toluene or xylene; or alternatively by heating from 50° C. to about 150° C. without any acidic agent and in the presence of an organic solvent only, e.g. toluene or xylene, if required.

A compound of formula (I) may be converted, as stated above, into another compound of formula (I) by known methods; for example, free hydroxy groups may be etherified by reaction with a suitable alkyl halide in the presence of a base such as NaH, $Na_2CO_3$, $K_2CO_3$, $NaNH_2$, sodium methoxide or sodium ethoxide in a solvent selected from the group consisting, for example, of methanol, ethanol, dioxane, acetone, dimethylformamide, hexamethylphosphorotriamide, tetrahydrofuran, water and their mixtures at a temperature ranging preferably between about 0° C. and about 150° C.

Furthermore, for example, a nitro-group as substituent in the $R_1$ phenyl group may be converted into an amino group by treatment, for example, with stannous chloride in concentrated hydrochloric acid, using, if necessary, an organic cosolvent such as acetic acid, dioxane, tetrahydrofuran at a temperature varying between room temperature and about 100° C.

For example, an amino or an hydroxy group may be converted into a formylamino, formyloxy, $C_2$-$C_8$ alkanoylamino or $C_2$-$C_8$ alkanoyloxy group, for example, respectively, by reaction with formic acid or with the corresponding alkanoyl anhydride without any solvent or in an organic solvent such as dioxane, dimethylformamide, tetrahydrofuran, usually in the presence of a base such as pyridine or triethylamine at a temperature varying between 0° C. and about 100° C.

As further example, a thiomorpholino group may be converted into a thiomorpholino 1-oxide group or into a thiomorpholino 1,1-dioxide group by reaction with suitable oxidizing agents, for example, with a stoichiometric amount of peracetic acid thus obtaining the 1-oxide derivatives or with m-chloroperbenzoic acid in $CH_2Cl_2$ thus obtaining the 1,1-dioxide derivatives, and carrying out the reaction in both the cases at a temperature varying between about 0° C. and about 30° C.

Also the optional salification of a compound of formula (I) as well as the conversion of a salt into a free compound and the separation of a mixture of isomers into the single isomers may be carried out by conventional methods.

For example the separation of a mixture of optical isomers into the individual isomers may be carried out by salification with an optically active acid and subsequent fractional crystallization.

The compounds of formula (II) may be obtained according to known methods; for example, the compounds of formula (II) wherein $R_7$ is a $-COR'_7$ group, wherein $R'_7$ is $C_1-C_{12}$ alkoxy or tri($C_1-C_6$)alkyl-silyloxy, may be prepared by cyclizing a compound of formula (IV)

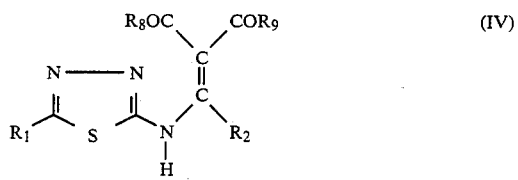

wherein $R_1$ and $R_2$ are as defined above and $R_8$ and $R_9$, which may be the same or different, are $C_1-C_2$ alkoxy or tri($C_1-C_6$)alkyl-silyloxy.

Analogous methods of preparation may be carried out for the other esters of formula (II).

The cyclization of a compound of formula (IV) may be, for example, carried out by treatment with an acid condensing agent such as polyphosphoric acid, alone or in the presence of phosphorus oxychloride, or by treatment with sulphuric or hydrochloric or acetic acid, methanesulphonic acid or p-toluenesulphonic acid, at a temperature ranging preferably between about 50° C. and 150° C.; the reaction may be carried out in an organic solvent such as dimethylformamide, dimethylacetamide, dimethylsulphoxide, formic acid, diglyme, toluene, xylene, ethylene glycol monomethylether or dichloroethane, but it is preferably carried out in the absence of a solvent.

Alternatively, the cyclization of a compound of formula (IV) may be carried out by heating the compound at a temperature ranging between about 150° C. and about 350° C., preferably between 200° C. and 300° C., in an inert high boiling organic solvent such as diphenyl ether or diglyme, or in the absence of a solvent.

The compounds of formula (IV) may be prepared, for example, by reacting a compound of formula (V)

wherein $R_1$ is as defined above, with a compound of formula (VI)

wherein $R_2$, $R_8$ and $R_9$ are as defined above and $R_{10}$ is a reactive group chosen, preferably, from hydroxy, amino, $C_1-C_6$ alkoxy or tri($C_1-C_6$)alkyl-silyloxy.

The reaction between a compound of formula (V) and a compound of formula (VI) may be carried out, for example, by heating in solvents such as dioxane, toluene, xylene, $C_1-C_4$ alkyl alcohol, dimethylformamide, dimethylacetamide, diglyme, diphenylether or in the absence of a solvent at a temperature varying from about 50° C. to about 200° C. Preferably, when $R_{10}$ is hydroxy, the reaction between a compound of formula (V) and a compound of formula (VI) is carried out in the presence of an acid condensing agent such as polyphosphoric acid, methanesulphonic acid, p-toluenesulphonic acid or acetic acid using the same experimental conditions as described above for the cyclization of the compounds of formula (IV).

The reaction of a compound of formula (V) with a compound of formula (VI) may be carried out till a compound of formula (II) is obtained without the need to isolate the intermediate product of formula (IV) formed during the reaction.

The compounds of formula (III), (V) and (VI) are known compounds or may be prepared by conventional methods: in some cases they are commercially available products.

When the reactions hereabove described concern compounds wherein free amino or hydroxy groups are present, the amino and hydroxy grouups may be protected, if necessary, in a conventional manner, before the reaction takes place. Amino protecting groups may be, for example, the protecting groups usually employed in the chemistry of peptides. Examples of amino protecting groups are formyl, an optional halo-substituted $C_2-C_6$ aliphatic acyl, preferably chloroacetyl, dichloroacetyl or trifluoroacetyl, tert-butoxycarbonyl, p-nitrobenzyloxy-carbonyl or trityl. The hydroxy groups may be protected, for example, by a formyl, acetyl, chloroacetyl, dichloroacetyl, trifluoroacetyl, tetrahydropyranyl, trityl or silyl group, preferably trimethylsilyl or dimethyl-tert.butyl silyl. The amino and hydroxy protecting groups are then removed at the end of the reaction, usually in a known manner. For example, when the amino protecting group is the monochloroacetyl group, it may be removed by treatment with thiourea; the formyl and the trifluoroacetyl groups may be removed by treatment with hydrochloric acid in aqueous methanol and the trityl group by treatment with formic or trifluoroacetic acid.

The hydroxy protecting groups, for instance, may be removed by mild reaction conditions, e.g. acid hydrolysis. The compounds of the present invention possess anti-inflammatory activity, as demonstrated e.g. by the fact that they are active, after oral administration, in inhibiting:
(A) the edema formation in the hind paw of rats in response to a subplantar injection of carrageenin, according to the method of C. A. Winter et al. (J. Pharmac. Exp. Therap. 1963, 141, 369) and P. Lence (Arch. Int. Pharmacodyn., 1962, 136, 237), and
(B) the Reversed Passive Arthus Reaction (RPAR) in rat paw, induced by the interaction of antigen and antibody resulting in the formation of precipitating immune complex, followed by fixation of complement and accumulation of polymorphonuclear leucocytes at a focal point (D. K. Gemmell, J. Cottney and A. J. Lewis, Agents and Actions 9/1 pag. 107, 1979).

The following Tables I and II show, for example, the approximate $ED_{50}$ values of the anti-inflammatory activity in the above mentioned tests, in the rat after oral administration, for a compound of this invention: 2-(3-pyridyl)-5-oxo-5H-1,3,4-thiadiazolo[3,2-a]pyrimidine-6-N-(2-pyridyl)-carboxamide (internal code FCE 22914):

TABLE I

| Compound | Anti-inflammatory activity Carrageenin induced oedema |
|---|---|
| FCE 22914 | $ED_{50}$ = 45.86 mg/kg |

TABLE II

| Compound | Anti-inflammatory activity RPAR reaction |
|---|---|
| FCE 22914 | $ED_{50}$ = 85.2 mg/kg |

The compounds of this invention are also endowed with analgesic activity.

The analgesic activity was assessed, for example, by means of the phenylquinone test in mice according to Siegmund: [Siegmund et al. Proc. Soc. Exper. Biol. Med. 95, 729 (1957)]. In this test the compound FCE 22914, for example, gives a 30% inhibition at 50 mg/kg after oral administration. It is known that certain thiadiazolo-pyrimidine derivatives are endowed with anti-allergic and anti-asthma activity, e.g. those described in Published Japan Patent Application No. J57 142989, but such compounds are devoid of any anti-inflammatory and/or analgesic activity. On the contrary the new thiadiazolo-pyrimidine derivatives of the present invention, which, as stated above, possess a therapeutically useful anti-inflammatory and analgesic activity, are surprisingly devoid of any anti-allergic and anti-asthma activity.

In view of their high therapeutic index, the compounds of the invention can be used safely in medicine. For example, the approximate acute toxicity ($LD_{50}$) of the compounds 2-(3-pyridyl)-5-oxo-5H-1,3,4-thiadiazolo[3,2-a]pyrimidine-6-N-(2-pyridyl)-carboxamide and 5-oxo-5H-1,3,4-thiadiazolo[3,2-a]pyrimidine-6-N-(2-pyridyl)-carboxamide in the mouse, determined by single administration of increasing doses and measured on the seventh day after treatment, is higher than 800 mg/kg per os. Analogous toxicity data have been found for other compounds of the invention.

The compounds of the invention can be administered in a variety of dosage forms, e.g. orally, in the form of tablets, capsules, sugar, or film coated tablets, liquid solutions or suspensions, rectally, in the form of suppositories, parenterally, e.g. intramuscularly or by intravenous injection or infusion.

The dosage depends on the age, weight, conditions of the patient and administration route; for example the dosage suitable for oral administration to adult humans for the treatment of pains and inflammatory processes ranges from about 10 to about 200 mg per dose, from 1 to 5 times daily. The invention includes pharmaceutical compositions comprising a compound of the invention in association with a pharmaceutically acceptable excipient (which can be a carrier or diluent).

The pharmaceutical compositions containing the compounds of the invention arre usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes. The liquid dispersion for oral administration may be e.g. syrups, emulsions and suspensions. The syrups may contain as carriers, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example, sorbitol. The suspensions and the emulsions may contain as carrier, for example, a natural gum, agar, sodium alginate, pectin, methylcellulose, carboxymethylcellulose or polyvinyl alcohol. The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carriers, for example, sterile water or preferably they may be in the form of sterile, aqueous, isotonic saline solutions.

The suppositories may contain together with the active compound a pharmaceutically acceptable carrier, e.g., cocoabutter, polyethylene glycol, a polyoxyethylene sorbitan fatty acid ester surfactant or lecithin. The following examples illustrate but do not limit the invention.

EXAMPLE 1

2-amino-1,3,4-thiadiazole (5 g) was reacted with diethyl ethoxymethylenemalonate (26.5 g) in ethanol (20 ml) at the reflux temperature for 23 hours. After cooling the precipitate was filtered and purified with hexane to give diethyl N-(1,3,4-thiadiazol-2-yl)-aminomethylenemalonate, m.p. 107°–111° C. (10 g), which was treated with polyphosphoric acid (57.6 g; 30.8 g of 99% $H_3PO_4$ and 26.8 g of $P_2O_5$) and $POCl_3$ (25 g) under stirring at 120° C. for 30 minutes.

After cooling the reaction mixture was diluted with ice water and then the solution was neutralized with 35% NaOH: the precipitate was filtered and washed with water to give 5-oxo-5H-1,3,4-thiadiazolo[3,2-a]pyrimidine-6-carboxylic acid, ethyl ester, m.p. 228°–230° C., (5.75 g), which was reacted with 2-amino-pyridine (4.9 g) in polyphosphoric acid (57.5 g: 31 g of 99% $H_3PO_4$ and 26.5 g of $P_2O_5$) under stirring at 120° C. for 12 hours. After cooling, dilution with ice water and neutralization with 35% NaOH, the precipitate was filtered and washed with water: crystallization from chloroform-methanol gave 3.3 g of 5-oxo-5H-1,3,4-thiadiazolo[3,2-a]pyrimidine-6-N-(2-pyridyl)-carboxamide, m.p. 240°–245° C. dec., NMR (DMSO d 6) δ p.p.m.: 7.15 (m) (1H, C-5 pyridyl proton), 7.84 (dt) (1H, C-4 pyridyl proton), 8.15–8.40 (m) (2H, C-3 and C-6 pyridyl protons), 8.92 (s) (1H, C-7 proton), 9.57 (1H, C-2 proton).

By proceeding analogously the following compounds were prepared:
2-methyl-5-oxo-5H-1,3,4-thiadiazolo[3,2-a]pyrimidine-6-N-(2-pyridyl)-carboxamide, m.p. 231°–233° C.;
2-ethyl-5-oxo-5H-1,3,4-thiadiazolo[3,2-a]pyrimidine-6-N-(2-pyridyl)-carboxamide, m.p. 247°–248° C.;
2-benzylthio-5-oxo-5H-1,3,4-thiadiazolo[3,2-a]pyrimidine-6-N-(2pyridyl)-carboxamide, m.p. 209°–211° C.;
2-methylthio-5-oxo-5H-1,3,4-thiadiazolo[3,2,-a]pyrimidine-6-N-(2-pyridyl)-carboxamide, m.p. 239°–240° C.,
2-ethylthio-5-oxo-5H-1,3,4-thiadiazolo[3,2-a]pyrimidine-6-N-(2-pyridyl)-carboxamide;
2-methylsulfinyl-5-oxo-5H-1,3,4-thiadiazolo[3,2-a]pyrimidine-6-N-(2-pyridyl)-carboxamide;
2-methylsulfonyl-5-oxo-5H-1,3,4-thiadiazolo[3,2-a]pyrimidine-6-N-(2-pyridyl)-carboxamide;
2-trifluoromethyl-5-oxo-5H-1,3,4-thiadiazolo[3,2-a]pyrimidine-6-N-(2-pyridyl)-carboxamide;
2-methoxymethyl-5-oxo-5H-1,3,4-thiadiazolo[3,2-a]pyrimidine-6-N-(2-pyridyl)-carboxamide, m.p. 218°–220° C.;
2-ethoxymethyl-5-oxo-5H-1,3,4-thiadiazolo[3,2-a]pyrimidine-6-N-(2-pyridyl)-carboxamide; and
2-chloro-5-oxo-5H-1,3,4-thiadiazolo[3,2-a]pyrimidine-6-N-(2-pyridyl)-carboxamide.

EXAMPLE 2

2-phenyl-5-oxo-5H-1,3,4-thiadiazolo[3,2-a]pyrimidine-6-carboxylic acid, ethyl ester, m.p. 172°–174° C. (3 g) was reacted with 2-amino-pyridine (1.9 g) in polyphosphoric acid (50 g: 26 g of 99% $H_3PO_4$ and 24 g of $P_2O_5$) under stirring at 110° C. for 6 hours. After cooling, dilution with ice water and neutralization with 35% NaOH, the precipitate was filtered and washed with water: crystallization from chloroform-ethanol gave 2.6 g of 2-phenyl-5-oxo-5H-1,3,4-thiadiazolo[3,2-a]pyrimidine-6-N-(2-pyridyl)-carboxamide, m.p. 273°–275° C., NMR ($CDCl_3CF_3COOD$) δ p.p.m.: 7.45–8.10 (m) (7H, C-3 and C-5 pyridyl protons and phenyl protons), 8.40 (m) (2H, C-4 and C-6 pyridyl protons), 9.10 (s) (1H, C-7 proton).

By proceeding analogously, the following compounds were prepared:
2-(4-fluoro-phenyl)-5-oxo-5H-1,3,4-thiadiazolo[3,2-a]pyrimidine-6-N-(2-pyridyl)-carboxamide, m.p. 214°–217° C.;
2-(4-chloro-phenyl)-5-oxo-5H-1,3,4-thiadiazolo[3,2-a]pyrimidine-6-N-(2-pyridyl)-carboxamide, m.p. 294°–297° C.;
2-(3-chloro-phenyl)-5-oxo-5H-1,3,4-thiadiazolo[3,2-a]pyrimidine-6-N-(2-pyridyl)-carboxamide;
2-(2-chloro-phenyl)-5-oxo-5H-1,3,4-thiadiazolo[3,2-a]pyrimidine-6-N-(2-pyridyl)-carboxamide;
2-(3,4-dichloro-phenyl)-5-oxo-5H-1,3,4-thiadiazolo[3,2-a]pyrimidine-6-N-(2-pyridyl)-carboxamide;
2-(4-methyl-phenyl)-5-oxo-5H-1,3,4-thiadiazolo[3,2-a]pyrimidine-6-N-(2-pyridyl)-carboxamide, m.p. 301°–303° C.;
2-(4-methoxy-phenyl)-5-oxo-5H-1,3,4-thiadiazolo[3,2-a]pyrimidine-6-N-(2-pyridyl)-carboxamide, m.p. 274°–278° C.;
2-(3-methoxy-phenyl)-5-oxo-5H-1,3,4-thiadiazolo[3,2-a]pyrimidine-6-N-(2-pyridyl)-carboxamide;
2-(4-nitro-phenyl)-5-oxo-5H-1,3,4-thiadiazolo[3,2-a]pyrimidine-6-N-(2-pyridyl)-carboxamide, m.p. 302°–305° C.;
2-(3-nitro-phenyl)-5-oxo-5H-1,3,4-thiadiazolo[3,2-a]pyrimidine-6-N-(2-pyridyl)-carboxamide;
2-(2-nitro-phenyl)-5-oxo-5H-1,3,4-thiadiazolo[3,2-a]pyrimidine-6-N-(2-pyridyl)-carboxamide;
2-(2-thienyl)-5-oxo-5H-1,3,4-thiadiazolo[3,2-a]pyrimidine-6-N-(2-pyridyl)-carboxamide, m.p. 270°–272° C.;
2-(4-N,N-dimethylamino-phenyl)-5-oxo-5H-1,3,4-thiadiazolo[3,2-a]pyrimidine-6-N-(2-pyridyl)-carboxamide; and
2-(3-N,N-dimethylamino-phenyl)-5-oxo-5H-1,3,4-thiadiazolo[3,2-a]pyrimidine-6-N-(2-pyridyl)-carboxamide.

EXAMPLE 3

2-amino-5-(3-pyridyl)-1,3,4-thiadiazole (10 g) was reacted with diethyl ethoxymethylene-malonate (18 g) under stirring at 120° C. for 9 hours. After cooling the reaction mixture was crystallized from $CH_2Cl_2$-isopropyl ether to give diethyl N-[5-(3-pyridyl)-1,3,4-thiadiazol-2-yl]-aminomethylene-malonate, m.p. 144°–145° C. (15.8 g) which was treated with polyphosphoric acid (6.6 g: 3.5 g of 99% $H_3PO_4$ and 3.1 g of $P_2O_5$) and $POCl_3$ (27.8 g) under stirring at 120° C. for 40 minutes.

After cooling the reaction mixture was diluted with ice water and then the reaction was neutralized with 35% NaOH. The precipitate was filtered and washed with water: crystallization from $CH_2Cl_2$-isopropyl alcohol gave 2-(3-pyridyl)-5-oxo-5H-1,3,4-thiadiazolo[3,2-a]pyrimidine-6-carboxylic acid, ethyl ester, m.p. 200°–202° C., (6.6 g), which was reacted with 2-amino-pyridine (10.02 g) in polyphosphoric acid (330 g: 176 g of 99% $H_3PO_4$ and 154 g of $P_2O_5$) under stirring at 120° C. for 7 hours. After cooling, dilution with ice water and neutralization with 35% NaOH, the precipitate was filtered and washed with water: crystallization from $CH_2Cl_2$-methanol gave 5.3 g of 2-(3-pyridyl)-5-oxo-5H-1,3,4-thiadiazolo[3,2-a]pyrimidine-6-N-(2-pyridyl)-carboxamide, m.p. 274°–277° C. NMR ($CDCl_3 + CF_3COOD$) δ ppm: 7.75 (m) (2H, C-5 pyridyl and C-5 pyridyl-amide protons), 8.45 (m) (3H, C-4 pyridyl and C-3 and C-4 pyridyl-amide protons), 9.20 (m) (2H, C-6 pyridyl and C-6 pyridyl-amide protons), 9.29 (s) (1H, C-7 proton), 9.67 (bs) (1H, C-2 pyridyl proton).

By proceeding analogously the following compounds were prepared:
2-morpholino-5-oxo-5H-1,3,4-thiadiazolo[3,2-a]pyrimidine-6-N-(2-pyridyl)-carboxamide, m.p. 274°–275° C., NMR ($CDCl_3 + CF_3COOD$) δ ppm: 3.4–4.0 (m) (8H, morpholinyl protons), 7.6 (m) (2H, C-4 and C-5 pyridyl protons), 8.3–8.6 (m) (2H, C-3 and C-6 pyridyl protons), 8.9 (s) (1H, C-7 proton);

2-(4-pyridyl)-5-oxo-5H-1,3,4-thiadiazolo[3,2-a]pyrimidine-6-N-(2-pyridyl)-carboxamide, m.p. 279°–280° C.;

2-(2-pyridyl)-5-oxo-5H-1,3,4-thiadiazolo[3,2-a]pyrimidine-6-N-(2-pyridyl)-carboxamide;

2-(3-pyridyl)-5-oxo-5H-1,3,4-thiadiazolo[3,2-a]pyrimidine-6-N-(6-methyl-2-pyridyl)-carboxamide, m.p. 305°–307° C.;

2-(3-pyridyl)-5-oxo-5H-1,3,4-thiadiazolo[3,2-a]pyrimidine-6-N-(5-methyl-2-pyridyl)-carboxamide;

2-(4-pyridyl)-5-oxo-5H-1,3,4-thiadiazolo[3,2-a]pyrimidine-6-N-(6-methyl-2-pyridyl)-carboxamide;

2-(4-pyridyl)-5-oxo-5H-1,3,4-thiadiazolo[3,2-a]pyrimidine-6-N-(4,6-dimethyl-2-pyridyl)-carboxamide;

2-(3-pyridyl)-5-oxo-5H-1,3,4-thiadiazolo[3,2-a]pyrimidine-6-N-(4,6-dimethyl-2-pyridyl)-carboxamide;

2-morpholino-5-oxo-5H-1,3,4-thiadiazolo[3,2-a]pyrimidine-6-N-(4,6-dimethyl-2-pyridyl)-carboxamide, m.p. 310°–313° C.;

2-morpholino-5-oxo-5H-1,3,4-thiadiazolo[3,2-a]pyrimidine-6-N-(5-chloro-2-pyridyl)-carboxamide, 2-morpholino-5-oxo-5H-1,3,4-thiadiazolo[3,2-a]pyrimidine-6-N-(3-pyridyl)-carboxamide;

2-(3-pyridyl)-5-oxo-5H-1,3,4-thiadiazolo[3,2-a]pyrimidine-6-N-(3-pyridyl)-carboxamide;

2-(3-pyridyl)-5-oxo-5H-1,3,4-thiadiazolo[3,2-a]pyrimidine-6-N-(5-chloro-2-pyridyl)-carboxamide, m.p. 306°–310° C.;

2-morpholino-5-oxo-5H-1,3,4-thiadiazolo[3,2-a]pyrimidine-6-N-(6-methyl-2-pyridyl)-carboxamide;

2-morpholino-5-oxo-5H-1,3,4-thiadiazolo[3,2-a]pyrimidine-6-N-(5-methyl-2-pyridyl)-carboxamide;

2-N,N-diethylamino-5-oxo-5H-1,3,4-thiadiazolo[3,2-a]pyrimidine-6-N-(2-pyridyl)-carboxamide;

2-N,N-dipropylamino-5-oxo-5H-1,3,4-thiadiazolo[3,2-a]pyrimidine-6-N-(2-pyridyl)-carboxamide;

2-N,N-diisopropylamino-5-oxo-5H-1,3,4-thiadiazolo[3,2-a]pyrimidine-6-N-(2-pyridyl)-carboxamide;

2-(pyrrolidin-1-yl)-5-oxo-5H-1,3,4-thiadiazolo[3,2-a]pyrimidine-6-N-(2-pyridyl)-carboxamide, m.p. 302°–304° C.;

2-piperidino-5-oxo-5H-1,3,4-thiadiazolo[3,2-a]pyrimidine-6-N-(2-pyridyl)-carboxamide, m.p. 242°–244° C.;

2-(2-methyl-piperidino)-5-oxo-5H-1,3,4-thiadiazolo[3,2-a]pyrimidine-6-N-(2-pyridyl)-carboxamide;

2-(3-methyl-piperidino)-5-oxo-5H-1,3,4-thiadiazolo[3,2-a]pyrimidine-6-N-(2-pyridyl)-carboxamide;

2-(4-methyl-piperidino)-5-oxo-5H-1,3,4-thiadiazolo[3,2-a]pyrimidine-6-N-(2-pyridyl)-carboxamide;

2-(2,6-dimethyl-piperidino)-5-oxo-5H-1,3,4-thiadiazolo[3,2-a]pyrimidine-6-N-(2-pyridyl)-carboxamide;

2-(3,5-dimethyl-piperidino)-5-oxo-5H-1,3,4-thiadiazolo[3,2-a]pyrimidine-6-N-(2-pyridyl)-carboxamide;

2-(2-ethyl-piperidino)-5-oxo-5H-1,3,4-thiadiazolo[3,2-a]pyrimidine-6-N-(2-pyridyl)-carboxamide;

2-(4-methyl-piperazin-1-yl)-5-oxo-5H-1,3,4-thiadiazolo[3,2-a]pyrimidine-6-N-(2-pyridyl)-carboxamide, m.p. 220°–221° C.;

2-(4-phenyl-piperazin-1-yl)-5-oxo-5H-1,3,4-thiadiazolo[3,2-a]pyrimidine-6-N-(2-pyridyl)-carboxamide;

2-[4-(2-pyridyl)-piperazin-1-yl]-5-oxo-5H-1,3,4-thiadiazolo[3,2-a]pyrimidine-6-N-(2-pyridyl)-carboxamide;

2-N,N-dibutylamino-5-oxo-5H-1,3,4-thiadiazolo[3,2-a]pyrimidine-6-N-(2-pyridyl)-carboxamide;

2-N,N-diisobutylamino-5-oxo-5H-1,3,4-thiadiazolo[3,2-a]pyrimidine-6-N-(2-pyridyl)-carboxamide;

2-(4-ethyl-piperazin-1-yl)-5-oxo-5H-1,3,4-thiadiazolo[3,2-a]pyrimidine-6-N-(2-pyridyl)-carboxamide;

5-oxo-5H-1,3,4-thiadiazolo[3,2-a]pyrimidine-6-N-(3-pyridyl)-carboxamide;

5-oxo-5H-1,3,4-thiadiazolo[3,2-a]pyrimidine-6-N-(5-chloro-2-pyridyl)-carboxamide, m.p. 260°–270° C. dec.;

2-methyl-5-oxo-5H-1,3,4-thiadiazolo[3,2-a]pyrimidine-6-N-(5-chloro-2-pyridyl)-carboxamide;

5-oxo-5H-1,3,4-thiadiazolo[3,2-a]pyrimidine-6-N-(6-methyl-2-pyridyl)-carboxamide, m.p. 258°–268° C. dec.;

5-oxo-5H-1,3,4-thiadiazolo[3,2-a]pyrimidine-6-N-(4,6-dimethyl-2-pyridyl)-carboxamide;

2-methyl-5-oxo-5H-1,3,4-thiadiazolo[3,2-a]pyrimidine-6-N-(6-methyl-2-pyridyl)-carboxamide;

2-methyl-5-oxo-5H-1,3,4-thiadiazolo[3,2-a]pyrimidine-6-N-(4,6-dimethyl-2-pyridyl)-carboxamide; and 2-morpholinomethyl-5-oxo-5H-1,3,4-thiadiazolo[3,2-a]pyrimidine-6-N-(2-pyridyl)-carboxamide.

EXAMPLE 4

2-amino-5-morpholino-1,3,4-thiadiazole (6.26 g) was reacted with diethyl ethoxymethylene-malonate (9 g) under stirring at 120° C. for 4 hours. After cooling the crude diethyl N-(5-morpholino-1,3,4-thiadiazol-2-yl)-aminomethylene-malonate was treated with polyphosphoric acid (5 g: 2.6 g of 99% $H_3PO_4$ and 2.4 g of $P_2O_5$) and $POCl_3$ (20.5 g) under stirring at 120° C. for 30 minutes.

After cooling the reaction mixture was diluted with ice water and then the solution was neutralized with 35% NaOH. The precipitate was filtered and washed with water: crystallization from $CH_2Cl_2$-isopropyl ether gave 2-morpholino-5-oxo-5H-1,3,4-thiadiazolo[3,2-a]pyrimidine-6-carboxylic acid, ethyl ester, m.p. 217°–219° C., (8 g), which was reacted with 2-amino-thiazole (5.2 g) in polyphosphoric acid (120 g: 64 g of 99% $H_3PO_4$ and 56 g of $P_2O_5$) under stirring at 110° C. for 30 hours. After cooling dilution with ice water and neutralization with 35% NaOH, the precipitate was filtered and washed with water: crystallization from $CH_2Cl_2$-ethanol gave 5 g of 2-morpholino-5-oxo-5H-1,3,4-thiadiazolo[3,2-a]pyrimidine-6-N-(2-thiazolyl)-carboxamide, m.p. 274°–276° C., NMR ($CDCl_3 + CF_3COOD$) δ ppm: 3.58 (m) (4H, C-3 and C-5 morpholinyl protons), 3.85 (m) (4H, C-2 and C-6 morpholinyl protons), 6.69 (d) (1H, C-5 thiazolyl proton), 7.75 (d) (1H, C-4 thiazolyl proton), 8.94 (s) (1H, C-7 proton).

By proceeding analogously the following compounds are prepared:

5-oxo-5H-1,3,4-thiadiazolo[3,2-a]pyrimidine-6-N-(4-methyl-2-thiazolyl)-carboxamide, m.p. 230°–240° C. dec.;

5-oxo-5H-1,3,4-thiadiazolo[3,2-a]pyrimidine-6-N-(4,5-dimethyl-2-thiazolyl)-carboxamide;

5-oxo-5H-1,3,4-thiadiazolo[3,2-a]pyrimidine-6-N-(1-methyl-3-pyrazolyl)-carboxamide;

5-oxo-5H-1,3,4-thiadiazolo[3,2-a]pyrimidine-6-N-(5-chloro-2-thiazolyl)-carboxamide, m.p. 255°–275° C. dec.;

5-oxo-5H-1,3,4-thiadiazolo[3,2-a]pyrimidine-6-N-(2-thiazolyl)-carboxamide, m.p. 230°–240° C. dec.;

5-oxo-5H-1,3,4-thiadiazolo[3,2-a]pyrimidine-6-N-(2-benzothiazolyl)-carboxamide, m.p. 162°–164° C.;
2-methyl-5-oxo-5H-1,3,4-thiadiazolo[3,2-a]pyrimidine-6-N-(2-thiazolyl)-carboxamide, m.p. 246°–249° C.;
2-(3-pyridyl)-5-oxo-5H-1,3,4-thiadiazolo[3,2-a]pyrimidine-6-N-(2-thiazolyl)-carboxamide, m.p. 322°–326° C.;
2-(4-pyridyl)-5-oxo-5H-1,3,4-thiadiazolo[3,2-a]pyrimidine-6-N-(2-thiazolyl)-carboxamide, m.p. 310°–316° C.;
2-(2-pyridyl)-5-oxo-5H-1,3,4-thiadizolo[3,2-a]pyrimidine-6-N-(2-thiazolyl)-carboxamide;
2-ethyl-5-oxo-5H-1,3,4-thiadiazolo[3,2-a]pyrimidine-6-N-(2-thiazolyl)-carboxamide, m.p. 239°–241° C.;
2-methyl-5-oxo-5H-1,3,4-thiadiazolo[3,2-a]pyrimidine-6-N-(1-methyl-3-pyrazolyl)-carboxamide;
2-methyl-5-oxo-5H-1,3,4-thiadiazolo[3,2-a]pyrimidine-6-N-(4,5-dimethyl-2-thiazolyl)-carboxamide;
2-methyl-5-oxo-5H-1,3,4-thiadiazolo[3,2-a]pyrimidine-6-N-(4-methyl-2-thiazolyl)-carboxamide;
2-(3-pyridyl)-5-oxo-5H-1,3,4-thiadiazolo[3,2-a]pyrimidine-6-N-(2-benzothiazolyl)-carboxamide;
2-(3-pyridyl)-5-oxo-5H-1,3,4-thiadiazolo[3,2-a]pyrimidine-6-N-(4-methyl-2-thiazolyl)-carboxamide;
2-(3-pyridyl)-5-oxo-5H-1,3,4-thiadiazolo[3,2-a]pyrimidine-6-N-(1-methyl-3-pyrazolyl)-carboxamide;
2-(4-pyridyl)-5-oxo-5H-1,3,4-thiadiazolo[3,2-a]pyrimidine-6-N-(4-methyl-2-thiazolyl)-carboxamide, m.p. 276°–279° C.;
2-(4-pyridyl)-5-oxo-5H-1,3,4-thiadiazolo[3,2-a]pyrimidine-6-N-(4,5-dimethyl-2-thiazolyl)-carboxamide, m.p. 330°–332° C.;
2-(4-pyridyl)-5-oxo-5H-1,3,4-thiadiazolo[3,2-a]pyrimidine-6-N-(5-chloro-2-thiazolyl)-carboxamide;
2-(4-pyridyl)-5-oxo-5H-1,3,4-thiadiazolo[3,2-a]pirimidine-6-N-(2-benzothiazolyl)-carboxamide;
2-morpholino-5-oxo-5H-1,3,4-thiadiazolo[3,2-a]pyrimidine-6-N-(4-methyl-2-thiazolyl)-carboxamide, m.p. 259°–261° C.;
2-morpholino-5-oxo-5H-1,3,4-thiadiazolo[3,2-a]pyrimidine-6-N-(2-benzothiazolyl)-carboxamide; m.p. 380°–385° C. dec.;
2-morpholino-5-oxo-5H-1,3,4-thiadiazolo[3,2-a]pyrimidine-6-N-(4,5-dimethyl-2-thiazolyl)-carboxamide, m.p. 325°–328° C.;
2-morpholino-5-oxo-5H-1,3,4-thiadiazolo[3,2-a]pyrimidine-6-N-(5-chloro-2-thiazolyl)-carboxamide, m.p. 279°–281° C.;
2-morpholino-5-oxo-5H-1,3,4-thiadiazolo[3,2-a]pyrimidine-6-N-(1-methyl-3-pyrazolyl)-carboxamide, m.p. 277°–279° C.;
2-(pyrrolidin-1-yl)-5-oxo-5H-1,3,4-thiadiazolo[3,2-a]pyrimidine-6-N-(2-thiazolyl)-carboxamide;
2-piperidino-5-oxo-5H-1,3,4-thiadiazolo[3,2-a]pyrimidine-6-N-(2-thiazolyl)-carboxamide, m.p. 249°–250° C.;
2-(4-methyl-piperazin-1-yl)-5-oxo-5H-1,3,4-thiadiazolo[3,2-a]pyrimidine-6-N-(2-thiazolyl)-carboxamide, m.p. 264°–266° C.;
2-(4-phenyl-piperazin-1-yl)-5-oxo-5H-1,3,4-thiadiazolo[3,2-a]pyrimidine-6-N-(2-thiazolyl)-carboxamide;
2-morpholinomethyl-5-oxo-5H-1,3,4-thiadiazolo[3,2-a]pyrimidine-6-N-(2-thiazolyl)-carboxamide;
2-(4-pyridyl)-5-oxo-5H-1,3,4-thiadiazolo[3,2-a]pyrimidine-6-N-(1-methyl-3-pyrazolyl)-carboxamide; and
2-[4-(2-pyridyl)-piperazin-1-yl]-5-oxo-5H-1,3,4-thiadiazolo[3,2-a]pyrimidine-6-N-(2-thiazolyl)-carboxamide.

EXAMPLE 5

2-amino-5-morpholino-1,3,4-thiadiazole (5 g) was reacted with diethyl(1-ethoxy-ethylidene)-malonate (6.2 g) in diglyme (40 ml) at 150° C. for 20 hours. After cooling the reaction mixture was diluted with ice water and extracted with ethyl acetate; after evaporation in vacuo to dryness, the residue was purified over a SiO$_2$ column using chloroform-methanol 98:2 as eluent. Crystallization from isopropyl ether gave 7-methyl-2-morpholino-5-oxo-5H-1,3,4-thiadiazolo[3,2-a]pyrimidine-6-carboxylic acid, ethyl ester, m.p. 196°–198° C. (2.6 g), which was reacted with 2-amino-pyridine (2.25 g) in polyphosphoric acid (130 g) under stirring at 120° C. for 4 hours. After cooling, dilution with ice water and neutralization with 35% NaOH, the precipitate was filtered and washed with water to give 1.9 g of 7-methyl-2-morpholino-5-oxo-5H-1,3,4-thiadiazolo[3,2-a]pyrimidine-6-N-(2-pyridyl)-carboxamide, m.p. 285°–287° C.

By proceeding analogously the following compounds were prepared:
7-methyl-5-oxo-5H-1,3,4-thiadiazolo[3,2-a]pyrimidine-6-N-(2-pyridyl)-carboxamide;
2,7-dimethyl-5-oxo-5H-1,3,4-thiadiazolo[3,2-a]pyrimidine-6-N-(2-pyridyl)-carboxamide;
2-ethyl-7-methyl-5-oxo-5H-1,3,4-thiadiazolo[3,2-a]pyrimidine-6-N-(2-pyridyl)-carboxamide;
7-methyl-2-methylthio-5-oxo-5H-1,3,4-thiadiazolo[3,2-a]pyrimidine-6-N-(2-pyridyl)-carboxamide;
2-benzylthio-7-methyl-5-oxo-5H-1,3,4-thiadiazolo[3,2-a]pyrimidine-6-N-(2-pyridyl)-carboxamide;
2-methoxymethyl-7-methyl-5-oxo-5H-1,3,4-thiadiazolo[3,2-a]pyrimidine-6-N-(2-pyridyl)-carboxamide;
2-ethoxymethyl-7-methyl-5-oxo-5H-1,3,4-thiadiazolo[3,2-a]pyrimidine-6-N-(2-pyridyl)-carboxamide;
7-ethyl-5-oxo-5H-1,3,4-thiadiazolo[3,2-a]pyrimidine-6-N-(2-pyridyl)-carboxamide;
7-methyl-2-(3-pyridyl)-5-oxo-5H-1,3,4-thiadiazolo[3,2-a]pyrimidine-6-N-(2-pyridyl)-carboxamide, m.p. 253°–255° C.;
7-ethyl-2-(3-pyridyl)-5-oxo-5H-1,3,4-thiadiazolo[3,2-a]pyrimidine-6-N-(2-pyridyl)-carboxamide;
7-methyl-2-(4-pyridyl)-5-oxo-5H-1,3,4-thiadiazolo[3,2-a]pyrimidine-6-N-(2-pyridyl)-carboxamide, m.p. 255°–256° C.;
2-N,N-diethylamino-7-methyl-5-oxo-5H-1,3,4-thiadiazolo[3,2-a]pyrimidine-6-N-(2-pyridyl)-carboxamide;
2-N,N-dipropylamino-7-methyl-5-oxo-5H-1,3,4-thiadiazolo[3,2-a]pyrimidine-6-N-(2-pyridyl)-carboxamide;
2-N,N-diisopropylamino-7-methyl-5-oxo-5H-1,3,4-thiadiazolo[3,2-a]pyrimidine-6-N-(2-pyridyl)-carboxamide;
7-methyl-2-(pyrrolidin-1-yl)-5-oxo-5H-1,3,4-thiadiazolo[3,2-a]pyrimidine-6-N-(2-pyridyl)-carboxamide;
7-methyl-2-(3-pyridyl-N-oxide)-5-oxo-5H-1,3,4-thiadiazolo[3,2-a]pyrimidine-6-N-(2-pyridyl)-carboxamide;
7-methyl-2-morpholino-5-oxo-5H-1,3,4-thiadiazolo[3,2-a]pyrimidine-6-N-(2-benzothiazolyl)-carboxamide;

7-methyl-2-piperidino-5-oxo-1,3,4-thiadiazolo[3,2-a]pyrimidine-6-N-(2-thiazolyl)-carboxamide;
7-methyl-2-(2-methyl-piperidino)-5-oxo-5H-1,3,4-thiadiazolo[3,2-a]pyrimidine-6-N-(2-pyridyl)-carboxamide;
7-methyl-2-(3-methyl-piperidino)-5-oxo-5H-1,3,4-thiadiazolo[3,2-a]pyrimidine-6-N-(2-pyridyl)-carboxamide;
7-methyl-2-(4-methyl-piperidino)-5-oxo-5H-1,3,4-thiadiazolo[3,2-a]pyrimidine-6-N-(2-pyridyl)-carboxamide;
2-(2,6-dimethyl-piperidino)-7-methyl-5-oxo-5H-1,3,4-thiadiazolo[3,2-a]pyrimidine-6-N-(2-pyridyl)-carboxamide;
7-methyl-2-(4-methyl-piperazin-1-yl)-5-oxo-5H-1,3,4-thiadiazolo[3,2-a]pyrimidine-6-N-(2-pyridyl)-carboxamide;
7-methyl-2-morpholinomethyl-5-oxo-5H-1,3,4-thiadiazolo[3,2-a]pyrimidine-6N-(2-pyridyl)-carboxamide;
7-methyl-2-(3-pyridyl)-5-oxo-5H-1,3,4-thiadiazolo[3,2-a]pyrimidine-6-N-(2-thiazolyl)-carboxamide, m.p. 322°–326° C.;
7-ethyl-2-morpholino-5-oxo-5H-1,3,4-thiadiazolo[3,2-a]pyrimidine-6-N-(2-pyridyl)-carboxamide;
7-ethyl-2-morpholino-5-oxo-5H-1,3,4-thiadiazolo[3,2-a]pyrimidine-6-N-(2-thiazolyl)-carboxamide;
7-methyl-2-(4-methyl-piperazin-1-yl)-5-oxo-5H-1,3,4-thiadiazolo[3,2-a]pyrimidine-6-N-(2-thiazolyl)-carboxamide;
7-methyl-2-[4-(2-pyridyl)-piperazin-1-yl]-5-oxo-5H-1,3,4-thiadiazolo[3,2-a]pyrimidine-6-N-(2-pyridyl)-carboxamide;
2-(thiomorpholino-1,1-dioxide)-7-methyl-5-oxo-5H-1,3,4-thiadiazolo[3,2-a]pyrimidine-6-N-(2-pyridyl)-carboxamide;
2-(thiomorpholino)-1,1-dioxide)-7-methyl-5-oxo-5H-1,3,4-thiadiazolo[3,2-a]pyrimidine-6-N-(2-thiazolyl)-carboxamide;
7-methyl-2-(4-pyridyl)-5-oxo-5H-1,3,4-thiadiazolo[3,2-a]pyrimidine-6-N-(2-thiazolyl)-carboxamide, m.p. 275°–277° C.;
7-methyl-2-morpholino-5-oxo-5H-1,3,4-thiadiazolo[3,2-a]pyrimidine-6-N-(2-thiazolyl)-carboxamide, m.p. 251°–254° C.;
7-methyl-5-oxo-5H-1,3,4-thiadiazolo[3,2-a]pyrimidine-6-N-(2-thiazolyl)-carboxamide;
2,7-dimethyl-5-oxo-5H-1,3,4-thiadiazolo[3,2-a]pyrimidine-6-N-(2-thiazolyl)-carboxamide;
7-methyl-2-(2-methyl-morpholino)-5-oxo-5H-1,3,4-thiadiazolo[3,2-a]pyrimidine-6-N-(2-pyridyl)-carboxamide; and
7-methyl-2-(4-pyridyl-N-oxide)-5-oxo-5H-1,3,4-thiadiazolo[3,2-a]pyrimidine-6-N-(2-thiazolyl)-carboxamide.

EXAMPLE 6

2-amino-5-(2-methyl-morpholino)-1,3,4-thiadiazole (10 g) was reacted with diethyl ethoxymethylenemalonate (11.3 g) at 120° C. for 30 minutes: after cooling the reaction mixture was crystallized from isopropyl ether to give diethyl N-[5-(2-methyl-morpholino)-1,3,4-thiadiazol-2-yl]-aminomethylene-malonate, m.p. 89°–91° C. (16.4 g), which was treated with polyphosphoric acid (6.9 g) and POCl$_3$ (27.15 g) under stirring at 120° C. for 30 minutes.

After cooling the reaction mixture was diluted with ice water and then the solution was neutralized with 35% NaOH: the precipitate was filtered and washed with water until neutral. Crystallization from CH$_2$Cl$_2$-isopropyl ether gave 2-(2-methyl-morpholino)-5-oxo-5H-1,3,4-thiadiazolo[3,2-a]pyrimidine-6-carboxylic acid, ethyl ester, m.p. 189°–191° C. (12.5 g), which was reacted with 2-amino-pyridine (11.2 g) in polyphosphoric acid (625 g: 320 g of 99% H$_3$PO$_4$ and 305 g of P$_2$O$_5$) under stirring at 120° C. for 8 hours. After cooling, dilution with ice water and neutralization with 35% NaOH, the obtained solution was extracted with ethyl acetate.

The organic phase was washed with water and then evaporated in vacuo to dryness: crystallization from CH$_2$Cl$_2$-methanol gave 7.6 g of 2-(2-methyl-morpholino)-5-oxo-5H-1,3,4-thiadiazolo[3,2-a]pyrimidine-6-N-(2-pyridyl)-carboxamide, m.p. 263°–265° C., NMR (CDCl$_3$+CF$_3$COOD) δ ppm: 1.33 (d) (3H,CH$_3$), 3.00–4.4 (m) (7H, morpholine protons), 7.6 (m) (2H, C-3 and C-5 pyridyl protons), 8.4 (m) (2H, C-2 and C-6 pyridyl protons), 9.0 (s) (1H, C-7 proton).

By proceeding analogously the following compounds were prepared:
2-(2-methyl-morpholino)-5-oxo-5H-1,3,4-thiadiazolo[3,2-a]pyrimidine-6-N-(6-methyl-2-pyridyl)-carboxamide;
2-(2-methyl-morpholino)-5-oxo-5H-1,3,4-thiadiazolo[3,2-a]pyrimidine-6-N-(5-methyl-2-pyridyl)-carboxamide;
2-(2-methyl-morpholino)-5-oxo-5H-1,3,4-thiadiazolo[3,2-a]pyrimidine-6-N-(4,6-dimethyl-2-pyridyl)-carboxamide;
2-(2-methyl-morpholino)-5-oxo-5H-1,3,4-thiadiazolo[3,2-a]pyrimidine-6-N-(1-methyl-3-pyrazolyl)-carboxamide;
2-(2-methyl-morpholino)-5-oxo-5H-1,3,4-thiadiazolo[3,2-a]pyrimidine-6-N-(2-thiazolyl)-carboxamide;
2-(2-methyl-morpholino)-5-oxo-5H-1,3,4-thiadiazolo[3,2-a]pyrimidine-6-N-(2-benzothiazolyl)-carboxamide;
2-(2-methyl-morpholino)-5-oxo-5H-1,3,4-thiadiazolo[3,2-a]pyrimidine-6-N-(4-methyl-2-thiazolyl)-carboxamide;
2-(2-methyl-morpholino)-5-oxo-5H-1,3,4-thiadiazolo[3,2-a]pyrimidine-6-N-(4,5-dimethyl-2-thiazolyl)-carboxamide;
2-(trans-2,6-dimethyl-morpholino)-5-oxo-5H-1,3,4-thiadiazolo[3,2-a]pyrimidine-6-N-(2-pyridyl)-carboxamide;
2-(cis-2,6-dimethyl-morpholino)-5-oxo-5H-1,3,4-thiadiazolo[3,2-a]pyrimidine-6-N-(2-pyridyl)-carboxamide, m.p. 272°–273° C., NMR (CDCl$_3$+CF$_3$COOD) δ: 1.26 (d) (6H, two —CH$_3$), 2.95 (m) (2H, C-3 and C-5 morpholinyl axial protons), 3.70 (m) (4H; C-3 and C-5 morpholinyl equatorial protons; C-2 and C-6 morpholinyl equatorial protons), 7.46 (dd) (1H, C-5 pyridyl proton), 8.0–8.4 (m) (2H, C-3 and C-4 pyridyl protons), 8.60 (bd) (1H, C-6 pyridyl proton), 8.82 (s) (1H, C-7 proton), 12.45 (bs) (1H, —CONH—) ppm;
2-(cis-2,6-dimethyl-morpholino)-5-oxo-5H-1,3,4-thiadiazolo[3,2-a]pyrimidine-6-N-(6-methyl-2-pyridyl)-carboxamide;
2-(cis-2,6-dimethyl-morpholino)-5-oxo-5H-1,3,4-thiadiazolo[3,2-a]pyrimidine-6-N-(5-methyl-2-pyridyl)-carboxamide;

2-(cis-2,6-dimethyl-morpholino)-5-oxo-5H-1,3,4-thiadiazolo[3,2-a]pyrimidine-6-N-(1-methyl-3-pyrazolyl)-carboxamide;

2-(cis-2,6-dimethyl-morpholino)-5-oxo-5H-1,3,4-thiadiazolo[3,2-a]pyrimidine-6-N-(4,6-dimethyl-2-pyridyl)-carboxamide;

2-(cis-2,6-dimethyl-morpholino)-5-oxo-5H-1,3,4-thiadiazolo[3,2-a]pyrimidine-6-N-(2-thiazolyl)-carboxamide;

2-(cis-2,6-dimethyl-morpholino)-5-oxo-5H-1,3,4-thiadiazolo[3,2-a]pyrimidine-6-N-(2-benzothiazolyl)-carboxamide;

2-(cis-2,6-dimethyl-morpholino)-5-oxo-5H-1,3,4-thiadiazolo[3,2-a]pyrimidine-6-N-(4-methyl-2-thiazolyl)-carboxamide;

2-(cis-2,6-dimethyl-morpholino)-5-oxo-5H-1,3,4-thiadiazolo[3,2-a]pyrimidine-6-N-(4,5-dimethyl-2-thiazolyl)-carboxamide;

2-thiomorpholino-5-oxo-5H-1,3,4-thiadiazolo[3,2-a]pyrimidine-6-N-(2-pyridyl)-carboxamide, m.p. 306°-308° C.;

2-thiomorpholino-5-oxo-5H-1,3-4-thiadiazolo[3,2-a]pyrimidine-6-N-(2-thiazolyl)-carboxamide;

2-(thiomorpholino-1-oxide)-5-oxo-5H-1,3,4-thiadiazolo[3,2-a]pyrimidine-6-N-(2-pyridyl)-carboxamide, m.p. 325°-330° C. (dec.);

2-(thiomorpholino-1-oxide)-5-oxo-5H-1,3,4-thiadiazolo[3,2-a]pyrimidine-6-N-(2-thiazolyl)-carboxamide, m.p. 365°-370° C. (dec.);

2-(thiomorpholino-1,1-dioxide)-5-oxo-5H-1,3,4-thiadiazolo[3,2-a]pyrimidine-6-N-(2-pyridyl)-carboxamide; m.p. 338°-340° C. (dec.);

2-(thiomorpholino-1,1-dioxide)-5-oxo-5H-1,3,4-thiadiazolo[3,2-a]pyrimidine-6-N-(2-benzothiazolyl)-carboxamide;

2-(thiomorpholino-1,1-dioxide)-5-oxo-5H-1,3,4-thiadiazolo[3,2-a]pyrimidine-6-N-(2-thiazolyl)-carboxamide;

2-(3-pyridyl-N-oxide)-5-oxo-5H-1,3,4-thiadiazolo[3,2-a]pyrimidine-6-N-(2-pyridyl)-carboxamide, m.p. 318°-320° C.;

2-(3-pyridyl-N-oxide)-5-oxo-5H-1,3,4-thiadiazolo[3,2-a]pyrimidine-6-N-(6-methyl-2-pyridyl)-carboxamide;

2-(3-pyridyl-N-oxide)-5-oxo-5H-1,3,4-thiadiazolo[3,2-a]pyrimidine-6-N-(2-thiazolyl)-carboxamide;

2-(4-pyridyl-N-oxide)-5-oxo-5H-1,3,4-thiadiazolo[3,2-a]pyrimidine-6-N-(2-thiazolyl)-carboxamide;

2-(4-pyridyl-N-oxide)-5-oxo-5H-1,3,4-thiadiazolo[3,2-a]pyrimidine-6-N-(2-benzothiazolyl)-carboxamide; and 2-(4-pyridyl-N-oxide)-5-oxo-5H-1,3,4-thiadiazolo[3,2-a]pyrimidine-6-N-(2-pyridyl)-carboxamide.

EXAMPLE 7

2-thiomorpholino-5-oxo-5H-1,3,4-thiadiazolo[3,2-a]pyrimidine-6-N-(2-pyridyl)-carboxamide (1.5 g) was reacted with peracetic acid obtained from 36% $H_2O_2$ (0.5 g) and acetic acid (70 ml) at room temperature for 1 hour. The reaction mixture was diluted with ice water, neutralized with $NaHCO_3$ and extracted with chloroform: the organic solution was washed with $H_2O$ and then evaporated in vacuo to dryness. Crystallization from $CH_2Cl_2$-methanol gave 0.8 g of 2-(thiomorpholino-1-oxide)-5-oxo-5H-1,3,4-thiadiazolo[3,2a]-pyrimidine-6-N-(2-pyridyl)-carboxamide, m.p. 325°-330° C. (dec.), NMR ($CDCl_3+CF_3COOD$) δ ppm: 3.30 (m) (4H, C-2 and C-6 thiomorpholinyl protons), 4.00-4.70 (m) (4H, C-3 and C-5 thiomorpholinyl protons), 7.70 (m) (2H, C-3 and C-5 pyridyl protons), 8.44 (m) (2H, C-4 and C-6 pyridyl protons), 9.11 (s) (1H, C-7 proton).

By proceeding analogously the following compound was prepared:

2-(thiomorpholino-1-oxide)-5-oxo-5H-1,3,4-thiadiazolo[3,2-a]pyrimidine-6-N-(2-thiazolyl)-carboxamide.

EXAMPLE 8

2-thiomorpholino-5-oxo-5H-1,3,4-thiadiazolo[3,2-a]pyrimidine-6-N-(2-thiazolyl)-carboxamide (1.3 g) was reacted with m-chloroperbenzoic acid (1.6 g) in methylene chloride (50 ml) at room temperature for 3 hours. The organic solution was washed with 5% $NaHCO_3$ solution and then with water: after evaporation in vacuo to dryness, crystallization from $CH_2Cl_2$-methanol gave 0.7 g of 2-(thiomorpholino-1,1-dioxide)-5-oxo-5H-1,3,4-thiadiazolo[3,2-a]pyrimidine-6-N-(2-thiazolyl)-carboxamide, m.p. 365°-370° C. (dec.).

By proceeding analogously the following compound was prepared:

2-(thiomorpholino-1,1-dioxide)-5-oxo-5H-1,3,4-thiadiazolo[3,2-a]pyrimidine-6-N-(2-benzothiazolyl)-carboxamide.

EXAMPLE 9

2-(4-nitro-phenyl)-5-oxo-5H-1,3,4-thiadiazolo[3,2-a]pyrimidine-6-N-(2-pyridyl)-carboxamide (4 g), prepared according to Example 2, was reacted with $SnCl_2.2H_2O$ (22.5 g) in 37% HCl (16 ml) and acetic acid (56 ml) under stirring at 60° C. for 8 hours. After cooling the precipitate was filtered and washed with acetic acid and then suspended under stirring in 2N NaOH: the product was filtered, washed with water until neutral and then crystallized from dioxane-ethanol to give 1.7 g of 2-(4-amino-phenyl)-5-oxo-5H-1,3,4-thiadiazolo[3,2-a]pyrimidine-6-N-(2-pyridyl)-carboxamide, m.p. 290°-293° C., NMR (DMOSO d6) δ ppm: 6.28 (bs) (2H, —NH$_2$), 6.70 (bd) (2H, C-3 and C-5 phenyl protons), 7.16 (m) (1H, C-5 pyridyl proton), 7.68 (bd) (2H, C-2 and C-6 phenyl protons), 7.84 (m) (1H, C-4 pyridyl proton), 8.20-8.40 (m) (2H, C-3 and C-6 pyridyl protons), 8.84 (s) (1H, C-7 proton), 11.40 (bs) (1H, —CONH—).

By proceeding analogously the following compounds were prepared:

2-(3-amino-phenyl)-5-oxo-5H-1,3,4-thiadiazolo[3,2-a]pyrimidine-6-N-(2pyridyl)-carboxamide;

2-(2-amino-phenyl)-5-oxo-5H-1,3,4-thiadiazolo[3,2-a]pyrimidine-6-N-(2-pyridyl)-carboxamide; and 2-(4-amino-phenyl)-7-methyl-5-oxo-5H-1,3,4-thiadiazolo[3,2-a]pyrimidine-6-N-(2-pyridyl)-carboxamide.

EXAMPLE 10

2-(4-amino-phenyl)-5-oxo-5H-1,3,4-thiadiazolo[3,2-a]pyrimidine-6-N-(2-pyridyl)-carboxamide (1.5 g), prepared according to Example 9, dissolved in dimethylformamide (20 ml), was reacted with acetic anhydride (4 ml) in the presence of pyridine (2 ml) at room temperature for 20 hours. The reaction mixture was diluted with ice water and the precipitate was filtered and washed with water: crystallization from dimethylformamide-methanol gave 1.2 g of 2-(4-N-acetyl-aminophenyl)-5-oxo-5H-1,3,4-thiadiazolo[3,2-a]pyrimidine-6-N-(2-pyridyl)-carboxamide.

By proceeding analogously the following compounds were prepared:

2-(3-N-acetyl-amino-phenyl)-5-oxo-5H-1,3,4-thiadiazolo[3,2-a]pyrimidine-6-N-(2-pyridyl)-carboxamide;

2-(2-N-acetyl-amino-phenyl)-5-oxo-5H-1,3,4-thiadiazolo[3,2-a]pyrimidine-6-N-(2-pyridyl)-carboxamide;

2-(4-N-formyl-amino-phenyl)-5-oxo-5H-1,3,4-thiadiazolo[3,2-a]pyrimidine-6-N-(2-pyridyl)-carboxamide; and 2-(4-N-acetyl-amino-phenyl)-7-methyl-5-oxo-5H-1,3,4-thiadiazolo[3,2-a]pyrimidine-6-N-(2-pyridyl)-carboxamide.

EXAMPLE 11

5-oxo-5H-1,3,4-thiadiazolo[3,2-a]pyrimidine-6-N-(2-pyridyl)-carboxamide (2 g) suspended in hot dioxane (500 ml) under stirring was treated with a slight excess of gaseous HCl dissolved in dioxane for 1 hour: after cooling the precipitate was filtered and washed with dioxane to give 2.1 g of 5-oxo-5H-1,3,4-thiadiazolo[3,2-a]pyrimidine-6-N-(2-pyridyl)-carboxamide, hydrochloride, m.p. >300° C. dec.

By proceeding analogously the following compounds were prepared:

2-methyl-5-oxo-5H-1,3,4-thiadiazolo[3,2-a]pyrimidine-6-N-(2-pyridyl)-carboxamide, hydrochloride;

2-(3-pyridyl)-5-oxo-5H-1,3,4-thiadiazolo[3,2-a]pyrimidine-6-N-(2-pyridyl)-carboxamide, hydrochloride;

2-morpholino-5-oxo-5H-1,3,4-thiadiazolo[3,2-a]pyrimidine-6-N-(2-pyridyl)-carboxamide, hydrochloride;

2-morpholino-5-oxo-5H-1,3,4-thiadiazolo[3,2-a]pyrimidine-6-N-(2-thiazolyl)-carboxamide, hydrochloride; and 2-(4-pyridyl)-5-oxo-5H-1,3,4-thiadiazolo[3,2-a]pyrimidine-6-N-(2-thiazolyl)-carboxamide, hydrochloride.

EXAMPLE 12

5-oxo-5H-1,3,4-thiadiazolo[3,2-a]pyrimidine-6-carboxylic acid, ethyl ester (2.25 g), prepared according to Example 1, was reacted with 4-chloro-aniline (1.95 g) in xylene (250 ml) at the reflux temperature for 18 hours carrying out a slow distillation of the solvent. After cooling the precipitate was filtered and washed with isopropyl ether: crystallization from ethanol gave 1.55 g of 5-oxo-5H-1,3,4-thiadiazolo[3,2-a]pyrimidine-6-N-(4-chloro-phenyl)-carboxamide.

By proceeding analogously the following compounds were prepared:

5-oxo-5H-1,3,4-thiadiazolo[3,2-a]pyrimidine-6-N-(4-methoxy-phenyl)-carboxamide;

5-oxo-5H-1,3,4-thiadiazolo[3,2-a]pyrimidine-6-N-(4-fluoro-phenyl)-carboxamide;

2-(3-pyridyl)-5-oxo-5H-1,3,4-thiadiazolo[3,2-a]pyrimidine-6-N-(4-chloro-phenyl)-carboxamide;

2-(3-pyridyl)-5-oxo-5H-1,3,4-thiadiazolo[3,2-a]pyrimidine-6-N-(4-methoxy-phenyl)-carboxamide;

2-morpholino-5-oxo-5H-1,3,4-thiadiazolo[3,2-a]pyrimidine-6-N-(4-chloro-phenyl)-carboxamide; and 2-morpholino-5-oxo-5H-1,3,4-thiadiazolo[3,2-a]pyrimidine-6-N-(4-methoxy-phenyl)-carboxamide.

EXAMPLE 13

Tablets, each weighing 150 mg and containing 50 mg of the active substance was manufactured as following:

| Compositions (for 10000 tablets) | |
| --- | --- |
| 2-(3-pyridyl)-5-oxo-5H—1,3,4-thiadiazolo[3,2-a] pyrimidine-6-N—(2-pyridyl)-carboxamide | 500 g |
| Lactose | 710 g |
| Corn starch | 237.5 g |
| Talc powder | 37.5 g |
| Magnesium stearate | 15 g |

2-(3-pyridyl)-5-oxo-5H-1,3,4-thiadiazolo[3,2-a]pyrimidine-6-N-(2-pyridyl)-carboxamide, lactose and a half of the corn starch were mixed; the mixture was then forced through a sieve of 0.5 mm openings. Corn starch (18 g) was suspended in warm water (180 ml). The resulting paste was used to granulate the powder. The granules were dried, comminuted on a sieve of sieve size 1.4 mm, then the remaining quantity of starch, talc and magnesium stearate was added, carefully mixed and processed into tablets using punches of 8 mm diameter.

By proceeding analogously tablets were prepared having the same composition, but containing as active substance one of the following compounds: 5-oxo-5H-1,3,4-thiadiazolo[3,2-a]pyrimidine-6-N-(2-pyridyl)-carboxamide, 2-morpholino-5-oxo-5H-1,3,4-thiadiazolo[3,2-a]pyrimidine-6-N-(2-pyridyl)-carboxamide and 7-methyl-2-morpholino-5-oxo-5H-1,3,4-thiadiazolo[3,2-a]pyrimidine-6-N-(2-pyridyl)-carboxamide.

EXAMPLE 14

Tablets, each weighing 150 mg and containing 50 mg of the active substance were manufactured as following:

| Compositions (for 10000 tablets) | |
| --- | --- |
| 2-(2-methyl-morpholino)-5-oxo-5H—1,3,4-thiadiazolo[3,2-a]pyrimidine-6-N—(2-pyridyl)-carboxamide | 500 g |
| Lactose | 710 g |
| Corn starch | 237.5 g |
| Talc powder | 37.5 g |
| Magnesium stearate | 15 g |

2-(2-methyl-morpholino)-5-oxo-5H-1,3,4-thiadiazolo[3,2-a]pyrimidine-6-N-(2-pyridyl)-carboxamide, lactose and a half of the corn starch were mixed; the mixture was then forced through a sieve of 0.5 mm openings. Corn starch (18 g) was suspended in warm water (180 ml). The resulting paste was used to granulate the powder. The granules were dried, comminuted on a sieve of sieve size 1.4 mm, then the remaining quantity of starch, talc and magnesium stearate was added, carefully mixed and processed into tablets using punches of 8 mm diameter.

By proceeding analogously, tablets were prepared having the same composition, but containing as active substance one of the following compounds:

2-(thiomorpholino-1,1-dioxide)-5-oxo-5H-1,3,4-thiadiazolo[3,2-a]pyrimidine-6-N-(2-pyridyl)-carboxamide and 7-methyl-2-(3-pyridyl)-5-oxo-5H-1,3,4-thiadiazolo[3,2-a]pyrimidine-6-N-(2-pyridyl)-carboxamide.

We claim:

1. A compound of general formula (I)

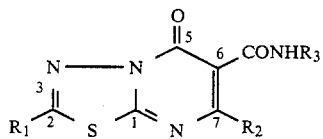

(1)

wherein
$R_1$ represents:
(a) a hydrogen or halogen atom or a $C_1-C_6$ alkyl group unsubstituted or substituted by $C_1-C_6$ alkoxy;
(b) a

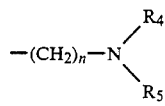

group, wherein n is zero, 1, 2 or 3 and each of $R_4$ and $R_5$ is, independently, hydrogen or $C_1-C_6$ alkyl, or $R_4$ and $R_5$, taken together with the nitrogen atom to which they are linked, form an unsubstituted N-pyrrolidinyl ring or a piperidino, morpholino, N-piperazinyl or

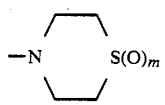

ring, wherein m is zero, 1 or 2, the piperidino and morpholino rings are unsubstituted or substituted by one or two $C_1-C_6$ alkyl groups and the N-piperazinyl ring is unsubstituted or substituted by a substituent chosen from $C_1-C_6$ alkyl, phenyl and pyridyl;
(c) trihalomethyl or a $R_6\text{-S(O)}_p$— group, wherein p is zero, 1 or 2 and $R_6$ is $C_1-C_6$ alkyl or benzyl, wherein the phenyl ring is unsubstituted or substituted by a substituent chosen from halogen, $C_1-C_6$ alkyl and $C_1-C_6$ alkoxy; or
(d) an unsubstituted pyridyl, pyridyl-N-oxide or thienyl ring or a phenyl ring unsubstituted or substituted by one, two or three substituents independently chosen from halogen, $C_1-C_6$ alkyl, $C_1-C_6$ alkoxy, hydroxy, formyloxy, $C_2-C_8$ alkanoyloxy, nitro, amino, formylamino, $C_2-C_8$ alkanoylamino and di-$(C_1-C_6)$alkyl-amino;

$R_2$ represents a hydrogen atom or a $C_1-C_6$ alkyl group;
$R_3$ represents:
(a') a phenyl ring, unsubstituted or substituted by one or two substituents independently chosen from $C_1-C_6$ alkyl, $C_1-C_6$ alkoxy and halogen;
(b') an unsaturated heteromonocyclic or heterobicyclic ring, containing one or more heteroatoms chosen from nitrogen and sulphur, unsubstituted or substituted by one or two substituents independently chosen from halogen, $C_1-C_6$ alkyl and $C_1-C_6$ alkoxy; and the pharmaceutically acceptable salts thereof.

2. A compound of formula (I), according to claim 1, wherein
$R_1$ is
(a'') hydrogen, $C_1-C_3$ alkyl, $C_1-C_3$ alkylthio, benzylthio, methoxymethyl, ethoxymethyl or di-$(C_1-C_4$ alkyl)amino; or
(b'') an unsubstituted N-pyrrolidinyl ring; a morpholino or piperidino ring, both unsubstituted or substituted by $C_1-C_2$ alkyl; or a N-piperazinyl ring substituted by a substituent chosen from $C_1-C_3$ alkyl, phenyl and pyridyl; or
(c'') an unsubstituted pyridyl or pyridyl-N-oxide ring; or a phenyl ring unsubstituted or substituted by one or two substituents chosen from chlorine, fluorine and methyl; or
(d'') a

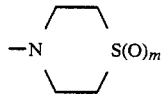

ring, wherein m is zero, 1 or 2;
$R_2$ is hydrogen or $C_1-C_2$ alkyl;
$R_3$ is an unsubstituted benzothiazolyl ring; 1-($C_1-C_4$ alkyl)pyrazolyl; or a thiazolyl or pyridyl ring, both unsubstituted or substituted by one or two substituents chosen from methyl and chlorine; and the pharmaceutically acceptable salts thereof.

3. A compound of formula (I), according to claim 1, wherein
$R_1$ is
(a''') hydrogen or methyl; or
(b''') an unsubstituted N-pyrrolidinyl ring; a piperidino or a morpholino ring, both unsubstituted or substituted by $C_1-C_2$ alkyl; or a N-piperazinyl ring substituted by a substituent chosen from $C_1-C_3$ alkyl, phenyl and pyridyl; or
(c''') an unsubstituted pyridyl or pyridyl-N-oxide ring; or
(d''')a

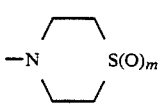

ring, wherein m is zero, 1 or 2;
$R_2$ is hydrogen or methyl;
$R_3$ is an unsubstituted benzothiazolyl ring; 1-($C_1-C_2$-alkyl)-pyrazolyl; or a thiazolyl or pyridyl ring, both unsubstituted or substituted by one or two methyl groups; and the pharmaceutically acceptable salts thereof.

4. A compound selected from the group consisting of:
5-oxo-5H-1,3,4-thiadiazolo[3,2-a]pyrimidine-6-N-(2-pyridyl)-carboxamide;
5-oxo-5H-1,3,4-thiadiazolo[3,2-a]pyrimidine-6-N-(2-thiazolyl)-carboxamide;
2-(4-pyridyl)-5-oxo-5H-1,3,4-thiadiazolo[3,2-a]pyrimidine-6-N-(2-benzothiazolyl)-carboxamide;
2-morpholino-5-oxo-5H-1,3,4-thiadiazolo[3,2-a]pyrimidine-6-N-(2-benzothiazolyl)-carboxamide;
2-morpholino-5-oxo-5H-1,3,4-thiadiazolo[3,2-a]pyrimidine-6-N-(2-thiazolyl)-carboxamide;
2-methyl-5-oxo-5H-1,3,4-thiadiazolo[3,2-a]pyrimidine-6-N-(2-pyridyl)-carboxamide;
2-morpholino-5-oxo-5H-1,3,4-thiadiazolo[3,2-a]pyrimidine-6-N-(2-pyridyl)-carboxamide;.

5-oxo-5H-1,3,4-thiadiazolo[3,2-a]pyrimidine-6-N-(2-benzothiazolyl)-carboxamide;

2-(3-pyridyl)-5-oxo-5H-1,3,4-thiadiazolo[3,2-a]pyrimidine-6-N-(2-pyridyl)-carboxamide;

2-(4-pyridyl)-5-oxo-5H-1,3,4-thiadiazolo[3,2-a]pyrimidine-6-N-(2-pyridyl)-carboxamide;

2-(4-pyridyl)-5-oxo-5H-1,3,4-thiadiazolo[3,2-a]pyrimidine-6-N-(2-thiazolyl)-carboxamide;

2-(2-methyl-morpholino)-5-oxo-5H-1,3,4-thiadiazolo[3,2-a]pyrimidine-6-N-(2-pyridyl)-carboxamide;

2-(4-methyl-piperazin-1-yl)-5-oxo-5H-1,3,4-thiadiazolo[3,2-a]pyrimidine-6-N-(2-pyridyl)-carboxamide;

2-(4-pyridyl)-5-oxo-5H-1,3,4-thiadiazolo[3,2-a]pyrimidine-6-N-(4-methyl-2-thiazolyl)-carboxamide;

2-(2-methyl-morpholino)-5-oxo-5H-1,3,4-thiadiazolo[3,2-a]pyrimidine-6-N-(2-thiazolyl)-carboxamide;

2-thiomorpholino-5-oxo-5H-1,3,4-thiadiazolo[3,2-a]pyrimidine-6-N-(2-pyridyl)-carboxamide;

7-methyl-2-morpholino-5-oxo-5H-1,3,4-thiadiazolo[3,2-a]pyrimidine-6-N-(2-pyridyl)-carboxamide;

7-methyl-2-morpholino-5-oxo-5H-1,3,4-thiadiazolo[3,2-a]pyrimidine-6-N-(2-thiazolyl)-carboxamide;

7-methyl-5-oxo-5H-1,3,4-thiadiazolo[3,2-a]pyrimidine-6-N-(2-pyridyl)-carboxamide;

7-methyl-5-oxo-5H-1,3,4-thiadiazolo[3,2-a]pyrimidine-6-N-(2-thiazolyl)-carboxamide;

2-(3-pyridyl-N-oxide)-5-oxo-5H-1,3,4-thiadiazolo[3,2-a]pyrimidine-6-N-(2-pyridyl)-carboxamide;

2-(4-pyridyl-N-oxide)-5-oxo-5H-1,3,4-thiadiazolo[3,2-a]pyrimidine-6-N-(2-thiazolyl)-carboxamide;

2-thiomorpholino-5-oxo-5H-1,3,4-thiadiazolo[3,2-a]pyrimidine-6-N-(2-thiazolyl)-carboxamide;

7-methyl-2-(3-pyridyl)-5-oxo-5H-1,3,4-thiadiazolo[3,2-a]pyrimidine-6-N-(2-pyridyl)-carboxamide;

7-methyl-2-(4-pyridyl)-5-oxo-5H-1,3,4-thiadiazolo[3,2-a]pyrimidine-6-N-(2-thiazolyl)-carboxamide;

2-(thiomorpholino-1,1-dioxide)-5-oxo-5H-1,3,4-thiadiazolo[3,2-a]pyrimidine-6-N-(2-pyridyl)-carboxamide;

2-(thiomorpholino-1,1-dioxide)-5-oxo-5H-1,3,4-thiadiazolo[3,2-a]pyrimidine-6-N-(2-thiazolyl)-carboxamide; and the pharmaceutically acceptable salts thereof.

5. A pharmaceutical composition containing a suitable carrier and/or diluent and, as an active principle, a compound of formula (I) according to claim 1, or a pharmaceutically acceptable salt thereof.

6. A method of treatment in a human patient of inflammatory processes and pains, said method comprising administering an effective amount of a compound of claim 1.

7. A method of treatment in a human patient of inflammatory processes and pains, said method comprising administering an effective amount of a pharmaceutical composition of claim 6.

* * * * *

UNITED STATES PATENT AND TRADEMARK OFFICE
CERTIFICATE OF CORRECTION

PATENT NO. : 4,522,944

DATED : June 11, 1985

INVENTOR(S) : DORIA et al

It is certified that error appears in the above-identified patent and that said Letters Patent is hereby corrected as shown below:

On the front page of the printed patent, left hand column, insert:

--Assignee: Farmitalia Carlo Erba S.p.A., Milan, Italy-- after the listing of the names of the two inventors.

Signed and Sealed this

Fourteenth Day of January 1986

[SEAL]

Attest:

DONALD J. QUIGG

Attesting Officer

Commissioner of Patents and Trademarks